United States Patent
Lee et al.

(10) Patent No.: US 8,759,514 B2
(45) Date of Patent: *Jun. 24, 2014

(54) METHOD FOR SEPARATION OF HMX AND RDX

(75) Inventors: Byoung-Min Lee, Seoul (KR); Youn-Woo Lee, Seoul (KR); Hyoun-Soo Kim, Daejeon (KR); Jung-Seob Shim, Daejeon (KR)

(73) Assignee: Agency for Defense Development, Daejeon (KR)

( * ) Notice: Subject to any disclaimer, the term of this patent is extended or adjusted under 35 U.S.C. 154(b) by 226 days.

This patent is subject to a terminal disclaimer.

(21) Appl. No.: 13/281,648

(22) Filed: Oct. 26, 2011

(65) Prior Publication Data

US 2012/0149896 A1 Jun. 14, 2012

(30) Foreign Application Priority Data

Dec. 14, 2010 (KR) .......................... 10-2010-0127896

(51) Int. Cl.
*C07D 257/02* (2006.01)

(52) U.S. Cl.
USPC ........................................................ 540/475

(58) Field of Classification Search
None
See application file for complete search history.

(56) References Cited

U.S. PATENT DOCUMENTS

| 5,389,263 A * | 2/1995 | Gallagher et al. ............. 210/729 |
| 2012/0276385 A1* | 11/2012 | Lee et al. ...................... 428/402 |

OTHER PUBLICATIONS

"Periodic Table", 2006, attached PDF.*

* cited by examiner

*Primary Examiner* — Noble Jarrell
(74) *Attorney, Agent, or Firm* — Scully, Scott, Murphy & Presser, P.C.

(57) ABSTRACT

The present invention is directed to a method for effectively separating HMX and RDX from HMX/RDX-included explosives, respectively, without using a harmful organic solvent, the method capable of respectively separating HMX and RDX from HMX/RDX-included explosives by selectively dissolving RDX included in explosives by using a difference between solubility parameters of HMX and RDX with respect to compressed dimethylether. The present invention is further directed to an apparatus for respectively separating HMX and RDX from HMX/RDX-included explosives comprising a dimethylether supplying unit, an explosive particle dissolving unit, and an explosive particle collecting unit.

8 Claims, 4 Drawing Sheets

METHOD FOR SEPARATION OF HMX AND RDX

CROSS-REFERENCE TO RELATED APPLICATION

Pursuant to 35 U.S.C. §119(a), this application claims the benefit of earlier filing date and right of priority to Korean Application No. 10-2010-0127896, filed on Dec. 14, 2010, the contents of which is incorporated by reference herein in its entirety.

BACKGROUND OF THE INVENTION

1. Field of the Invention

This specification relates to a method for separation of HMX and RDX, and particularly, to a method for effectively separating HMX and RDX from HMX/RDX-included explosives, respectively.

2. Background of the Invention

Explosives having a high performance and being widely used in many fields include HMX (Cyclotetramethylenetetranitramine) and RDX (Cyclotrimethylenetrinitramine). Each of the HMX and RDX is presented in a state of impurities by a certain amount in a synthesis process. For instance, when HMX is synthesized by the Bachmann process, RDX is also synthesized by about 27%. This requires an additional separation.

In order to obtain HMX of a high purity through an additional separation, a mixture of HMX and RDX (HMX explosives mixed with 27% RDX) is put in a solution where 2.93 g of sodium tetraborate ($Na_2B_4O_7$ or $Na_2B_4O_7 \cdot 10H_2O$) was dissolved in 975.6 g of water. Then, the mixture is boiled with being agitated. Then, 5N sodium hydroxide is added to 42.4 cc of the solution with a speed of 3 mL/min (for 47.3 minutes). The solution is continuously boiled, and sodium hydroxide is put to increase pH to 9.7 from 8.7. As a result, pure HMX having RDX completely separated from the mixture is obtained. Then, the mixture is re-crystallized by using a solvent (nitromethane, acetone, acetonitrile, cyclohexanone, etc.), thereby forming pure HMX particles having a 'β'-form.

In order to more easily separate HMX or RDX generated in the form of impurities during a synthesis process, a supercritical separation process has been proposed. A supercritical fluid is defined as 'any substance at a temperature and pressure above its critical point', and has a unique characteristic not exhibited in the conventional solvent. A physical property of a solvent is determined by an intermolecular interaction determined by a molecule type and a molecule distance. Since a liquid solvent is a non-compressed type, an intermolecular distance is scarcely changed. Accordingly, it is difficult to expect a great change of a property from the liquid solvent used as a single solvent. A density of the supercritical fluid may be consecutively changed from highly rarefied conditions close to an ideal gas to a high density close to a liquid density. Therefore, this may control not only an equilibrium property (solubility, entrainer effects) of a fluid, a transfer property (viscosity, diffusion coefficient, thermal conductivity), but also dissolution (solvation) and a molecule clustering state. A supercritical fluid process is performed to maximize energy usage efficiency during extraction, separation and drying processes, by selectively separating a product having a high purity and a high value at a high transfer speed based on excellent thermodynamic characteristics (spontaneous separation due to high solubility, selectivity, compressibility, and decompression), flowing characteristics (low viscosity and surface tension, and high diffusion coefficient), by re-using an extracted solvent, by removing a solvent remaining on the product, etc.

There has been proposed a method for separation of HMX and RDX by dissolving a mixture including HMX and RDX in heated water and a heated solvent of cyclopentanon, and then by performing selective re-crystallization. Alternatively, there has been proposed a method for separation of HMX by dissolving a mixture of RDX and HMX in a solvent of dimethyl sulfoxide having a temperature of 70~90° C., by adding a sufficient amount of water to the mixture, and by performing re-crystallization. Still alternatively, there has bee proposed a method for forming β-HMX by dissolving acetic anhydride/HMX slurry in an acid remaining after performing nitrolysis with respect to hexamine, and by performing re-crystallization.

In the aforementioned methods for separation of HMX and RDX, selective re-crystallization was performed by using an organic solvent, an acetate solution, an aqueous solution or a mixture thereof. However, these methods may have the following problems. Firstly, an organic solvent harmful to a human body has to be used. Secondly, a liquid chromatograph absorption method causing a large amount of waste water has to be used. Thirdly, these methods are not suitable for massive productions.

SUMMARY OF THE INVENTION

Therefore, an aspect of the detailed description is to provide a method for effectively separating HMX and RDX from HMX/RDX-included explosives, respectively, without using a harmful organic solvent, the method capable of respectively separating HMX and RDX from HMX/RDX-included explosives by selectively dissolving RDX included in explosives by using a difference between solubility parameters of HMX and RDX with respect to compressed dimethylether.

To achieve these and other advantages and in accordance with the purpose of this specification, as embodied and broadly described herein, a method for separation of HMX and RDX including (1) putting HMX/RDX-included explosives in a container, (2) introducing dimethylether into the container, thereby forming an RDX solution where the RDX of the explosives has been dissolved, (3) collecting the HMX by filtering the RDX solution, and crystallizing the RDX included in the RX solution by discharging the RDX solution to atmospheric pressure, thereby forming RDX particles, and (4) collecting the RDX particles.

An apparatus for respectively separating HMX and RDX from HMX/RDX-included explosives may include a dimethylether supplying unit, an explosive particle dissolving unit, and an explosive particle collecting unit. The dimethylether supplying unit may include a high pressure container, a supplying pipe connected to the explosive particle dissolving unit from the high pressure container, a high pressure pump, and a back pressure regulator (BPR) positioned at an end of the supplying pipe. The explosive particle dissolving unit may include a pre-heater, a high-pressure dissolver, a first filter and an agitator. And, the explosive particle collecting unit may include a particle collecting container, an injection nozzle connected to the particle collecting container, and a second filter.

The present invention may have the following advantages.

Firstly, HMX may be separated from HMX/RDX-included explosives by selectively dissolving the RDX with using a compressed gas, dimethylether. This may allow HMX of a high purity to be obtained.

Secondly, the dimethylether used as a solvent in the present invention may have a non-toxic property and an eco-friendly property, and may be re-used by being collected after fine particles have been manufactured. This may be very advantageous in an economic aspect.

Thirdly, an organic solvent and water may not be used differently from the conventional art. Accordingly, there may occur no waste water, and a large number of separations may be performed within a short time.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed to description.

BRIEF DESCRIPTION OF THE DRAWINGS

The accompanying drawings, which are included to provide a further is understanding of the invention and are incorporated in and constitute a part of this specification, illustrate exemplary embodiments and together with the description serve to explain the principles of the invention.

In the drawings.

DETAILED DESCRIPTION OF THE INVENTION

Figure 1:
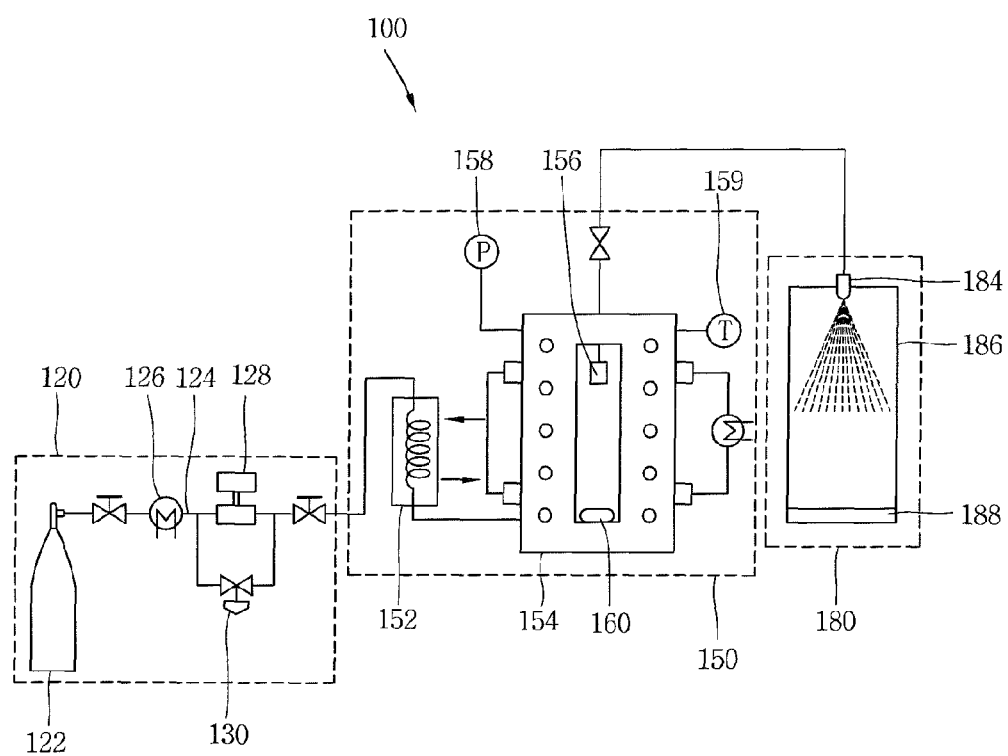
FIG. 1 is a view showing a rapid expansion of supercritical solutions (RESS) apparatus applied to separate HMX and RDX according to one embodiment of the present invention.

Description will now be given in detail of the exemplary embodiments, with reference to the accompanying drawings. For the sake of brief description with reference to the drawings, the same or equivalent components will be provided with the same reference numbers, and description thereof will not be repeated.

A method for separation of HMX and RDX according to the present invention includes (1) putting HMX/RDX-included explosives in a container, (2) introducing dimethylether into the container, thereby forming an RDX solution where the RDX of the explosives has been dissolved, (3) collecting the HMX by filtering the RDX solution, and crystallizing the RDX included in the RDX solution by discharging the RDX solution to atmospheric pressure, thereby forming RDX particles, and (4) collecting the RDX particles.

In order to separate HMX, RDX is preferably dissolved by using a rapid expansion of supercritical solutions (RESS) apparatus.

Compressed dimethylether is introduced in explosives including HMX and RDX. The RDX included in the explosives is dissolved by a difference between solubility parameters of HMX and RDX with respect to the compressed dimethylether. Then, the RDX-dissolved dimethylether is discharged to atmospheric pressure, thereby filtering and collecting undissolved HMX. The discharged RDX is precipitated to be obtained as crystallized particles. The HMX separated from the explosives is in a state of particles including RDX of a low composition, and the RDX is also in a state of high-purity particles scarcely including HMX. These particles may include a small amount of hetero particles, but may include pure HMX and RDX by being dissolved in a compressed gas, dimethylether and then by undergoing the above processes. Since an organic solvent and water are not used, there occurs no waste water and a large number of separations are performed within a short time.

As the dimethylether used in the step (2), a liquid or a compressed gas may be used. For implementation of non-combustibility including a small amount of low explosives so as to reduce an explosion risk, may be alternatively used one or more gases selected from a group consisting of dimethylether, HFC-23, HFC-125, HFC-236fa, HFC-227ea, Perfluoromethane, Perfluoroethane, Perfluoropropane, Perfluorobutane, $CF_3I$ and $CO_2$, rather than exclusively using dimethylether.

The dimethylether used in the step (2) may have a temperature of 0~200° C., and a pressure of 2.5~800 bar. In the temperature range, 0° C. indicates a lower limitation of a solubility of explosives (no productivity). And, 200° C. indicates an upper limitation with consideration of explosions of explosives. When the pressure is below 2.5 bar, an operation cannot be performed. And, when the pressure is above 800 bar, high costs are required during processes.

For enhancement of a purity and efficiency, the solution discharged in the step (3) may be cooled and compressed to undergo the step (2) again.

An apparatus for respectively separating HMX and RDX from HMX/RDX-included explosives according to the present invention includes a dimethylether supplying unit, an explosive particle dissolving unit, and an explosive particle collecting unit. The dimethylether supplying unit includes a high pressure container, a supplying pipe connected to the explosive particle dissolving unit from the high pressure container, a high pressure pump, and a back pressure regulator positioned at an end of the supplying pipe. The explosive particle dissolving unit includes a pre-heater, a high-pressure dissolver, a first filter and an agitator. The explosive particle collecting unit includes a particle collecting container, an injection nozzle connected to the particle collecting container, and a second filter. The apparatus further includes a second gas supplying unit for supplying additional gas. And, the second gas supplying unit includes a second high to pressure container, a second supplying pipe connected to the explosive particle dissolving unit from the second high pressure container, a second high pressure pump, and a second back pressure regulator positioned at an end of the second supplying pipe.

Hereinafter, the present invention will be explained in more details with is reference to the attached drawings. The present invention is not limited to the apparatus and method implemented in the attached drawings.

FIG. 1 is a view showing a rapid expansion of supercritical solutions (RESS) apparatus applied to separate HMX and RDX according to one embodiment of the present invention.

As shown in FIG. 1, the RESS apparatus 100 according to the present invention includes a dimethylether supplying unit 120, an explosive particle dissolving unit 150, and an explosive particle collecting unit 180.

The dimethylether supplying unit 120 includes a high pressure container 122 for dimethylether, a connecting line 124, a pre-cooler 126, a high pressure pump 128, and a back pressure regulator 130. The high pressure container 122 for dimethylether is a storage container for containing dimethylether, a solvent for dissolving RDX. The connecting line 124 serves to supply the dimethylether contained in the high pressure container 122 for dimethylether to the explosive particle dissolving unit 150. The pre-cooler 126 is disposed on the connecting line, and serves to cool the dimethylether so as to smoothly operate the high pressure pump 128. The high pressure pump 128 is disposed on a connecting line, and serves to firstly apply a pressure so that the supplied dimethylether can be in a supercritical state, a high-pressure liquid state, or a compressed gas state. The back pressure regulator 130 is disposed at a connecting line parallel to the high pressure pump, and serves to constantly maintain a pressure of the dissolving unit to while the consecutively-compressed dimethylether is supplied to the explosive particle dissolving unit 150 and the explosive particle collecting unit 180. Although not shown, the apparatus may further include a second gas supplying unit for additionally supplying gas such as HFC-23, HFC-125, HFC-236fa, HFC-227ea, Perfluoromethane, Perfluoroethane, Perfluoropropane, Perfluororobutane, $CF_3I$ and $CO_2$.

The explosive particle dissolving unit 150 includes a pre-heater 152, a high-pressure dissolver, a first filter 156, a pressure controller 130 and an agitator 160. The pre-heater 152 is configured to encompass a part of the connecting line, and serves to heat compressed dimethylether (compressed gas, dimethylether) provided through the connecting line to a predetermined temperature. The high-pressure dissolver 154 is configured to accommodate therein explosives including the HMX and RDX, and to implement a space where the RDX is dissolved into the compressed dimethylether. The first filter 156 serves to transmit the RDX-dissolved compressed dimethylether, and to filter HMX undissolved in the compressed dimethylether from the explosives thus to obtain only pure HMX particles. A pressure gauge 158 maintains an internal state of the high-pressure dissolver 154 as a high pressure state, and secondarily compresses the dimethylether compressed by the high pressure pump so as to have a high pressure or a supercritical state. The thermometer 159 measures a temperature inside the high pressure dissolver 154. Here, the compressed dimethylether preferably has a temperature of 0~200° C., and a pressure of 2.5~800 bar.

The explosive particle collecting unit 180 includes an injection nozzle 184, a particle collecting container 186, and a second filter 188. The particle collecting container 186 implements a space where RDX-dissolved dimethylether is introduced from the high-pressure dissolver, and the dissolved RDX particles are crystallized (precipitated). The injection nozzle is provided in the particle collecting container 186, and is configured to discharge compressed dimethylether having passed therethrough into the particle collecting container having a low pressure, thereby crystallizing (precipitating) RDX particles having a fine size. The second filter is provided in the particle collecting container so that the dimethylether gas may serve to filter the crystallized fine RDX particles.

Figure 2:
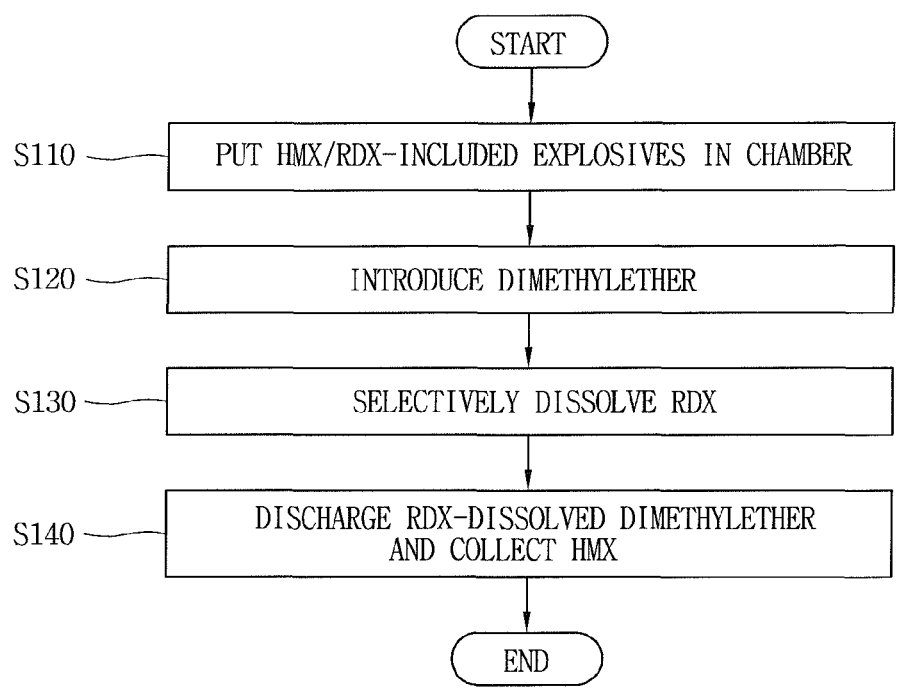
FIG. 2 is a flowchart showing a method for separation of HMX and RDX according to one embodiment of the present invention.

FIG. 2 is a flowchart showing a method for separation of HMX and RDX according to one embodiment of the present invention.

As shown in FIG. 2, HMX/RDX-included explosives is put into a rapid expansion of supercritical solutions (RESS) apparatus (S110).

In S110, the explosives may be manufactured through an explosive synthesis process for manufacturing HMX or RDX. The explosives manufactured through the synthesis process include both HMX and RDX, since HMX and RDX are generated together even if one type of explosive particles are synthesized. The explosives are introduced into the high-pressure dissolver 154 of the RESS (rapid expansion of supercritical solutions) apparatus shown in FIG. 1.

Then, compressed dimethylether is provided to the HMX/RDX-included explosives (S120).

In S120, the dimethylether may be provided to the explosives by being introduced into the high-pressure dissolver 154 by the dimethylether supplying unit 120 shown in FIG. 1. More concretely, the dimethylether is maintained as a liquid state by the high pressure pump 128 and the back pressure regulator 130, and then is introduced into the high-pressure dissolver 154 through a connecting line. The compressed dimethylether introduced into the high-pressure dissolver 154 has a temperature of 0~200° C., and a pressure of 2.5~800 bar.

As another embodiment, a compressed dimethylether mixed gas rather to than the dimethylether may be introduced into the high-pressure dissolver. As the compressed dimethylether mixed gas, may be used a compressed mixed gas of dimethylether and at least one gas selected from a group consisting of HFC-23, HFC-125, HFC-236fa, HFC-227ea, Perfluoromethane, Perfluoroethane, Perfluoropropane, Perfluororobutane, $CF_3I$ and $CO_2$.

Then, only the RDX included in the explosives is dissolved by the compressed dimethylether (S130).

The dimethylether compressed in S130 may dissolve only RDX among the explosives present in the high-pressure dissolver 154. Accordingly, only RDX-dissolved dimethylether, and HMX dispersed in the dimethylether are present in the high-pressure dissolver.

Then, the RDX-dissolved dimethylether is discharged to atmospheric pressure to obtain RDX particles, and the HMX present in the high-pressure dissolver is filtered to obtain HMX particles (S140).

The HMX filtration in S140 is a process for separating only HMX particles by using the first filter provided in the high-pressure dissolver. As the HMX particles are separated by the first filter, the RDX-dissolved dimethylether may be discharged to the air through the first filter thus to be separated from the HMX. The method for separation of HMX and RDX according to the present invention is based on a difference between solubility parameters with respect to a solvent, which will be theoretically explained as follows.

A solubility parameter is used to easily and rapidly predict an interaction between a solvent and a solute. Generally, when a difference ($\delta_1-\delta_2$) between a solubility parameter of a solvent and a solubility parameter of a solute is less than 1.7~2.0 ($\delta_1-\delta_2<1.7$~2.0), a probability to dissolve the solute in the solvent is high. Solubility parameters were calculated so as to mathematically approach a phenomenon that HMX is not dissolved but RDX is dissolved in dimethylether, a solvent having a high pressure.

The solubility parameters of HMX and RDX were calculated by using the following Fedors Equation (1). The solubility parameters of RDX and HMX calculated by the Fedors Equation were 10.49 and 11.08, respectively (under a is temperature condition of 25° C. and a pressure condition of 1.013 bar). In order to calculate changes of solubility parameters of HMX and RDX according to a temperature change, a change of a solubility parameter of RDX was calculated by using the following equation (2).

$$\delta_1\left(\frac{cal}{cm^3}\right)^{1/2} = \left(\frac{\sum_i (\Delta E_V)_i}{\sum_i (\Delta V)_i}\right) \quad (1)$$

$$\delta_2\left(\frac{cal}{cm^3}\right)^{1/2} = \delta_1\left(\frac{V_1}{V_2}\right)^{1.13} = \delta_1\left(\frac{\rho_2}{\rho_2}\right)^{1.13} = \delta_1\left(\frac{T_c - T_2}{T_c - T_1}\right)^{0.33} \quad (2)$$

Figure 3:
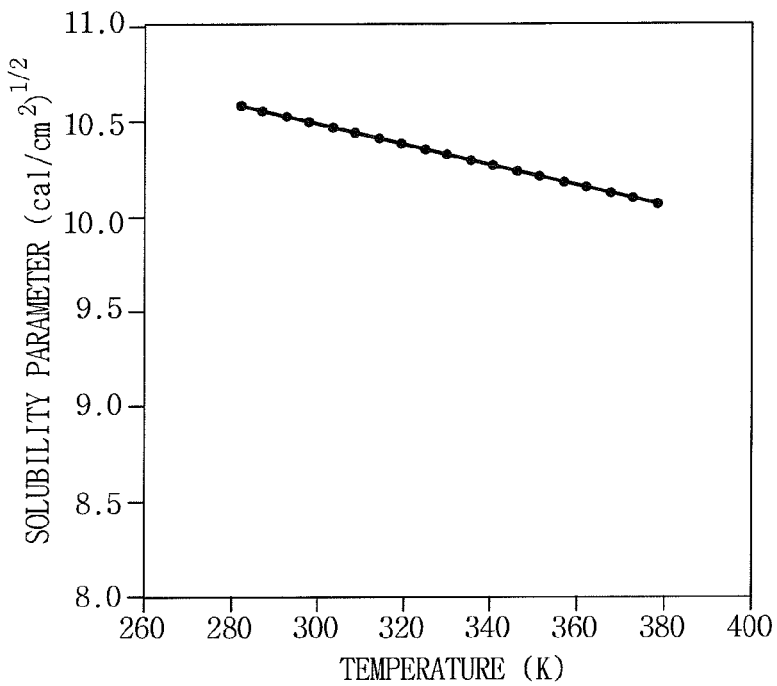
FIG. 3 is a graph showing a solubility parameter change of RDX according to a temperature change.

FIG. 3 is a graph showing a solubility parameter change of RDX depending on a temperature change.

A high pressure fluid including a supercritical fluid has a solubility parameter changed according to a temperature and a pressure. Accordingly, the following equation (3) proposed by Giddings is being used.

$$\delta_1\left(\frac{cal}{cm^3}\right)^{1/2} = 1.25(P_o)^{1/2}\left(\frac{\rho_{\gamma,SF}}{\rho_{\gamma,L}}\right) \quad (3)$$

Figure 4:
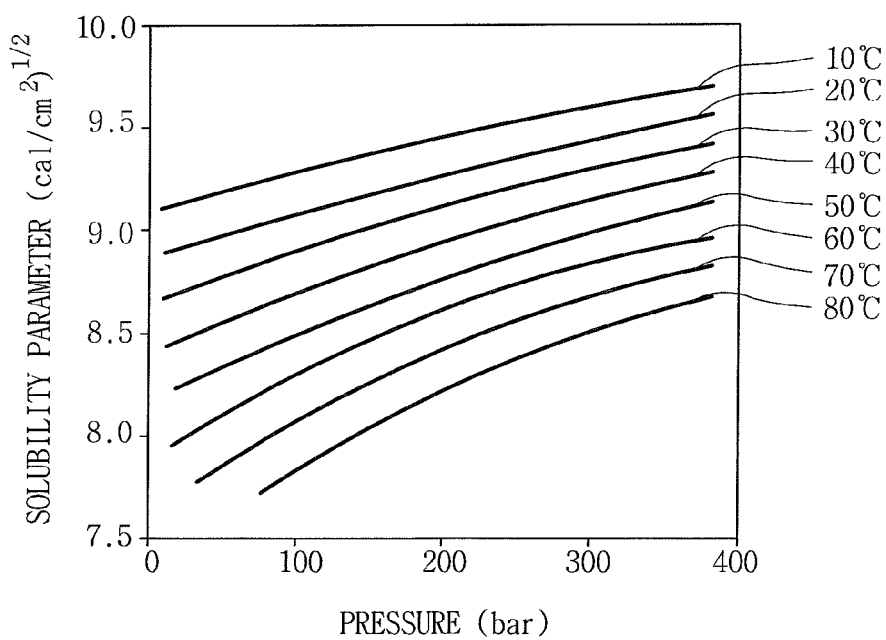
FIG. 4 is a graph showing a solubility parameter change of dimethylether according to changes of a temperature and a pressure.

FIG. 4 is a graph showing a solubility parameter change of dimethylether according to changes of a temperature and a pressure.

As shown in FIG. 4, a solubility parameter of dimethylether is decreased as a temperature is increased, but is increased as a pressure is increased.

Figure 5:
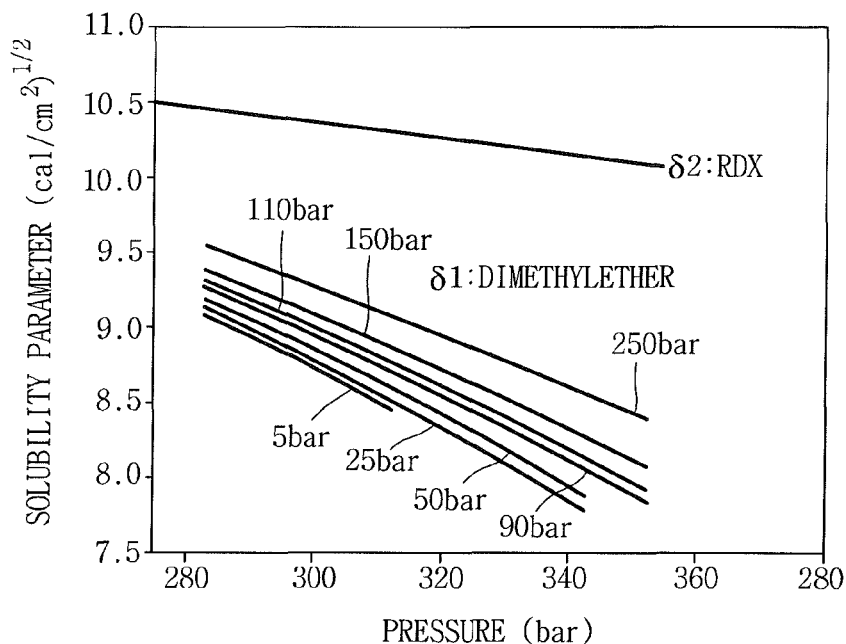
FIG. 5 is a graph showing a correlation between solubility parameters of RDX and dimethylether.

FIG. 5 is a graph showing a correlation between solubility parameters of RDX and dimethylether.

As can be seen from the graph of FIG. 5, a difference between solubility parameters of compressed dimethylether and RDX does not exceed two. This may indicate that RDX was dissolved in dimethylether of a high pressure. When considering that the solubility parameter of RDX is not drastically deceased according to a temperature change, the solubility parameter of HMX, 11.08 at a temperature of 25° C. is not greatly changed even if a temperature is increased. Accordingly, it is analyzed that the HMX was not dissolved in the compressed dimethylether, since the difference ($\delta_1-\delta_2$) between solubility parameters of the compressed dimethylether and the HMX is more than two.

Each solubility of RDX and HMX according to changes of a temperature and a pressure was measured by using the apparatus of FIG. 1, the apparatus having compressed dimethylether applied thereto. 10 mg of HMX was put in the high-pressure dissolver, and a compressed gas, dimethylether having a temperature of 60° C. and a pressure of 200 bar was put therein. As a measurement result with respect to solubility, the HMX was scarcely dissolved in spite of lapses of several hours. On the other hand, when 400 mg of RDX was dissolved in 80 g of dimethylether, a compressed gas having a temperature of 40° C. and a pressure of 150 bar, the RDX was completely dissolved within about 20 minutes. This may indicate that the compressed gas, dimethylether is a solvent suitable for a supercritical separation process for separating explosive particles by a difference between a solubility of HMX and a solubility of RDX.

HMX and RDX were separated from a reaction mixture by using a supercritical fluid processing apparatus having a compressed gas, dimethylether applied thereto. Here, only RDX was dissolved by using dimethylether having a temperature of 0~200° C. and a pressure of 2.5~800 bar.

Figure 6:
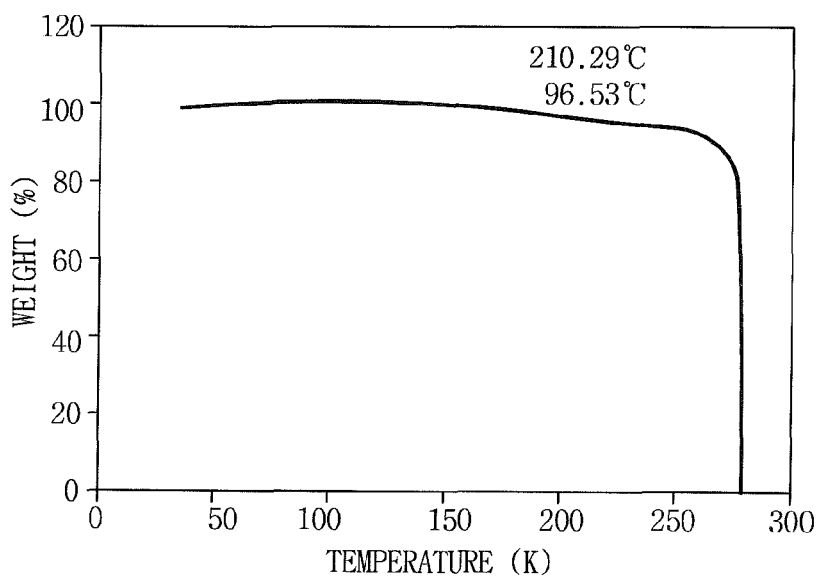
FIG. 6 is a graph showing a thermal analysis result of HMX particles separated by the method according to one embodiment of the present invention.

A purity of HMX particles separated by this method was analyzed by using to a differential scanning thermo-gravimetric analyzer (TGA), which was shown in FIG. 6. FIG. 6 is a graph showing a thermal analysis result of HMX particles separated by the method according to one embodiment of the present invention.

Before the separation, the HMX particles contained 27% impurity RDX. However, as can be seen from FIG. 6, the impurity RDX was rescued to 3.5% thus to obtain HMX having a purity of 96.5%.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A method for separation of HMX and RDX, comprising:
   (1) putting HMX/RDX-included explosives in a container;
   (2) introducing dimethylether solvent into the container, thereby forming an RDX solution where the RDX of the explosives has been dissolved;
   (3) collecting the HMX by filtering the RDX solution, and crystallizing the RDX included in the RDX solution by discharging the RDX solution to atmospheric pressure, thereby forming RDX particles; and
   (4) collecting the RDX particles.

2. The method of claim 1, wherein the dimethylether in step (2) is introduced in a state of a liquid or compressed gas.

3. The method of claim 1, wherein the dimethylether in step (2) is implemented as a mixture of dimethylether and at least one gas selected from a group consisting of dimethylether, HFC-23, HFC-125, HFC-236fa, HFC-227ea, Perfluoromethane, Perfluoroethane, Perfluoropropane, Perfluororobutane, $CF_3I$ and $CO_2$.

4. The method of claim 1, wherein the dimethylether used in the step (2) has a temperature of 0~200° C., and a pressure of 2.5~800 bar.

5. The method of claim 1, wherein the solution discharged in step (3) is cooled and compressed to undergo the step (2) again.

6. An apparatus comprising:
   a dimethylether supplying unit;
   an explosive particle dissolving unit; and
   an explosive particle collecting unit,
   wherein the dimethylether supplying unit has a high pressure container, a supplying pipe connected to the explosive particle dissolving unit from the high pressure container, a high pressure pump, and a back pressure regulator (BPR) positioned at an end of the supplying pipe,
   wherein the explosive particle dissolving unit has a preheater, a high-pressure dissolver, a first filter and an agitator, and
   wherein the explosive particle collecting unit has a particle collecting container, an injection nozzle connected to the particle collecting container, and a second filter.

7. The apparatus of claim 6, further comprising a second gas supplying unit for supplying additional gas, wherein the second gas supplying unit has a second high pressure container, a second supplying pipe connected to the explosive particle dissolving unit from the second high pressure container, a second high pressure pump, and a second back pressure regulator positioned at an end of the second supplying pipe.

8. The apparatus of claim 6, wherein the apparatus is configured to separate HMX and RDX from HMX/RDX-included explosives.

* * * * *